United States Patent [19]

Yoshioka et al.

[11] Patent Number: 5,651,869
[45] Date of Patent: Jul. 29, 1997

[54] BIOSENSOR

[75] Inventors: Toshihiko Yoshioka, Osaka; Shin Ikeda, Katano; Shiro Nankai, Hirakata, all of Japan

[73] Assignee: Matsushita Electric Industrial Co., Ltd., Kadoma, Japan

[21] Appl. No.: 605,391

[22] Filed: Feb. 22, 1996

[30] Foreign Application Priority Data

Feb. 28, 1995 [JP] Japan .................................. 7-040157
Mar. 30, 1995 [JP] Japan .................................. 7-072585

[51] Int. Cl.⁶ ............................ G01N 27/26; C12Q 1/64
[52] U.S. Cl. .......................... 204/403; 435/817; 435/14
[58] Field of Search .................... 435/817, 14; 204/403

[56] References Cited

U.S. PATENT DOCUMENTS

| | | | |
|---|---|---|---|
| 5,081,037 | 1/1992 | Kariyone et al. | 435/288 |
| 5,192,416 | 3/1993 | Yoshioka et al. | 204/403 |
| 5,264,103 | 11/1993 | Yoshioka et al. | 204/403 |

FOREIGN PATENT DOCUMENTS

| | | |
|---|---|---|
| 0114747 | 10/1987 | Japan . |
| 63-294799 | 12/1988 | Japan . |
| 64-059056 | 3/1989 | Japan . |
| 2-062958 | 3/1990 | Japan . |
| 3-202764 | 9/1991 | Japan . |
| 5-196595 | 8/1993 | Japan . |

OTHER PUBLICATIONS

Abstract of JP 05196595 (Yoshinobu Tokundo) Aug. 6, 1993.
Abstract of JP 02062958 (Karigome et al.) Mar. 2, 1990.
Abstract of JP 01114747 (Matsushita Electric) Oct. 29, 1987.
Abstract of JP 6459056 (Shigeo Kobayashi) Mar. 6, 1989.
Search Report for European Patent Application No. 96102861.0 dated Sep. 5, 1996.
Chemical Abstracts, vol. III, No. 25, Dec. 18, 1989, Columbus, Ohio, USA, S. Tajima et al. "Simultaneous Determination of Glucose and 1,5-any-Droglucitrol" p. 394, No. 228, 556 J; & JPN, Kokai Koha, 1988 No month available. JP-A-63-294 799 (88 294799).

Primary Examiner—Kathryn L. Gorgos
Assistant Examiner—Alex Noguerola
Attorney, Agent, or Firm—Renner, Otto, Boisselle & Sklar

[57] ABSTRACT

The biosensor of this invention includes an electrically insulating substrate; an electrode system formed on the substrate which includes a working electrode and a counter electrode; and a reaction layer formed on the substrate or above the substrate with a space therebetween. The reaction layer includes a pyranose-oxidizing enzyme.

13 Claims, 2 Drawing Sheets

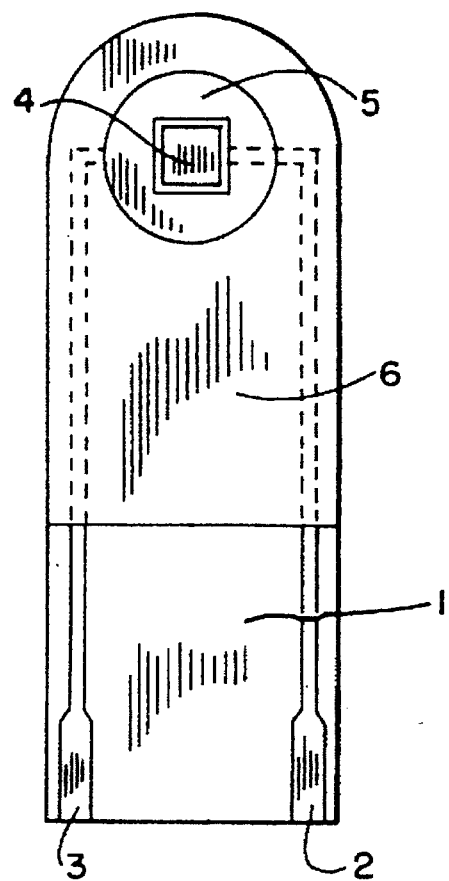
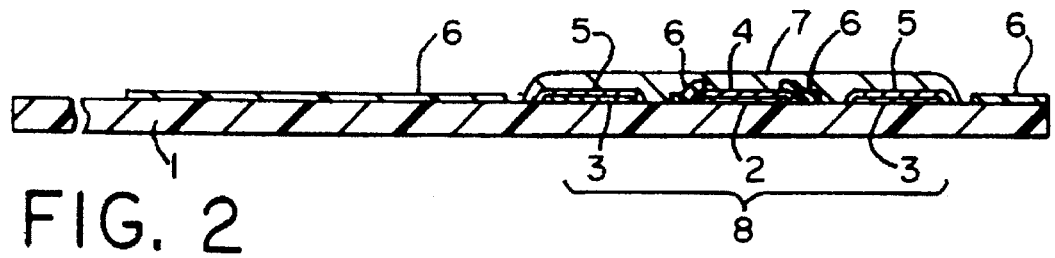
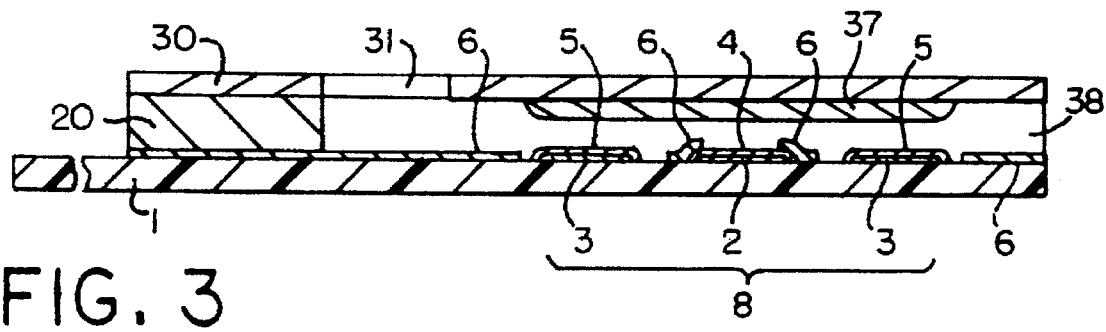

BIOSENSOR

BACKGROUND OF THE INVENTION

1. Field of the Invention

The present invention relates to a biosensor for quantitating a substrate (specific component) contained in a sample liquid such as whole blood, plasma, serum, urine, fruit juice and the like, with accuracy, speed and ease. More particularly, the invention relates to a glucose sensor for electrochemically measuring a concentration of glucose included in a sample liquid by reacting the glucose with an oxidoreductase which can react with specificity to the glucose.

2. Description of the Related Art

Various methods such as an optical rotation method, a colorimetric method, a reductimetry method and other methods which use different kinds of chromatographies have been developed as methods for the quantitative analysis of a saccharide such as sucrose and glucose. However, none of these methods has sufficiently high accuracy because the specificity thereof against saccharides is not very high. Among these methods, the optical rotation method can be easily conducted but is known to be significantly influenced by the operating temperature.

Recently, various types of biosensors have been developed which can easily quantitate a specific component (substrate) in a sample liquid such as a biological sample and food without diluting and stirring the sample liquid.

For example, Japanese Laid-Open Patent Publication No. 3-202764 discloses a biosensor comprising an electrode system formed on an insulating substrate by screen printing or the like and a reaction layer formed on the electrode system and including a hydrophilic polymer, an oxidoreductase, and an electron acceptor. The concentration of a substrate in a sample liquid is measured by using this biosensor as follows. First, the sample liquid is dropped on the reaction layer of the biosensor, so as to dissolve the reaction layer. This causes an enzyme reaction between the substrate in the sample liquid and the oxidoreductase in the reaction layer, and then, the electron acceptor in the reaction layer is reduced. After the completion of the enzyme reaction, the reduced electron acceptor is electrochemically oxidized, thereby measuring the concentration of the substrate in the sample liquid based on an oxidation current value obtained in this oxidation.

U.S. Pat. No. 5,192,415 discloses a biosensor comprising a hydrogen ion concentration control layer which can optimize the pH of the sample liquid depending upon the type of oxidoreductase contained in a reaction layer without previously adjusting the pH of a sample liquid.

U.S. Pat. No. 5,264,103 discloses a biosensor comprising a main electrode system formed on an electrically insulating substrate and including a working electrode and a counter electrode; a reaction layer including an oxidoreductase; and a sub electrode layer provided with an interval from the main electrode system and including a working electrode and a counter electrode.

These biosensors can be used in a wide range of applications, for example as, a glucose sensor, an alcohol sensor, a cholesterol sensor, or an amino acid sensor by appropriately selecting an oxidoreductase to be contained in the reaction layer.

Among these biosensors, a glucose sensor is generally known to include glucose oxidase as the oxidoreductase. Such a glucose sensor has, however, the following problem.

Among isomers of glucose, glucose oxidase reacts to β-glucose alone which exists at a proportion of 63% in the equilibrium state. Therefore, a response current value (i.e., detection sensitivity) obtained by such a glucose sensor is so small that measurement error is large, for example, in quantitating an extremely small amount of glucose.

In addition, when this glucose sensor is used to quantitate polysaccharides, most of the glucose produced by a hydrolase is α-glucose, and hence, an additional procedure is required, before the quantitation, for isomerizing α-glucose produced through the hydrolysis into β-glucose by using a mutarotase.

Japanese Patent Application No. 6-291401 (unpublished) relates to a biosensor including both mutarotase and glucose oxidase. In this biosensor, however, the detection sensitivity cannot be sufficiently improved when the total amount of these enzymes is small, and the production cost is increased when the total amount of the enzymes is large. Furthermore, when the concentration of a substrate in a sample liquid is comparatively high, the biosensor including mutarotase and glucose oxidase has lower detection sensitivity as compared with a biosensor excluding mutarotase.

SUMMARY OF THE INVENTION

The biosensor of the present invention comprises an electrically insulating substrate; an electrode system formed on the substrate which includes a working electrode and a counter electrode; and a reaction layer formed on the substrate or above the substrate with a space therebetween. The reaction layer includes a pyranose-oxidizing enzyme.

In one embodiment, the pyranose-oxidizing enzyme is pyranose oxidase (EC1.1.3.10).

In another embodiment, the reaction layer further includes glucose oxidase (EC1.1.3.4).

In still another embodiment, the reaction layer further includes an electron acceptor.

In still another embodiment, the electron acceptor is a ferricyanide ion.

In still another embodiment, the reaction layer further includes polysaccharide hydrolase.

In still another embodiment, the polysaccharide hydrolase is one selected from the group consisting of sucrose hydrolase, maltose hydrolase, and lactose hydrolase.

In one embodiment, the content of the pyranose-oxidizing enzyme is 1 to about 200 units per 1 $cm^2$ of the reaction layer.

In still another embodiment, the content of the pyranose-oxidizing enzyme is about 0.1 to about 200 units per 1 $cm^2$ of the reaction layer.

In still another embodiment, the contents of the pyranose-oxidizing enzyme and the ferricyanide ion are 1 to about 200 units and about 0.21 mg to about 3.30 mg, respectively per 1 $cm^2$ of the reaction layer.

In still another embodiment, the contents of the pyranose-oxidizing enzyme, the glucose oxidase and the ferricyanide ion are about 0.1 to about 200 units, 1 to about 200 units, and about 0.21 mg to about 3.30 mg, respectively per 1 $cm^2$ of the reaction layer.

In one embodiment, the biosensor is used for measuring a blood glucose level.

Alternatively, the biosensor of the present invention, for quantitating a substrate included in a sample liquid by reducing an electron acceptor with an electron generated through an enzyme reaction of the substrate and electrochemically measuring an amount of a reduced form of the electron acceptor, comprises an electrically insulating substrate; an electrode system formed on the substrate and including a working electrode and a counter electrode; and a reaction layer formed on the substrate or above the substrate with a space therebetween. The reaction layer includes a pyranose-oxidizing enzyme and the electron acceptor.

In one embodiment, the reaction layer further includes glucose oxidase (EC1.1.3.4).

In another embodiment, the biosensor is a glucose sensor.

In still another embodiment, the biosensor is used for measuring a blood glucose level.

Thus, the invention described herein makes possible the advantages of (1) providing a biosensor which can measure the concentration of a substrate in a sample liquid with accuracy and speed by simultaneously detecting α-glucose and β-glucose; (2) providing a biosensor which can easily measure the concentration of a substrate in a sample liquid including polysaccharide; and (3) providing a biosensor which can be manufactured at a low cost.

These and other advantages of the present invention will become apparent to those skilled in the art upon reading and understanding the following detailed description with reference to the accompanying figures.

BRIEF DESCRIPTION OF THE DRAWINGS

FIG. 1 is a schematic plane view of a biosensor as an example of the invention in which a reaction layer is omitted;

FIG. 2 is a schematic sectional view of a biosensor as an example of the invention in which a reaction layer is directly disposed on a substrate;

FIG. 3 is a schematic sectional view of a biosensor as another example of the invention in which a reaction layer is disposed above a substrate with a space therebetween;

DESCRIPTION OF PREFERRED EMBODIMENTS

Figure 4:
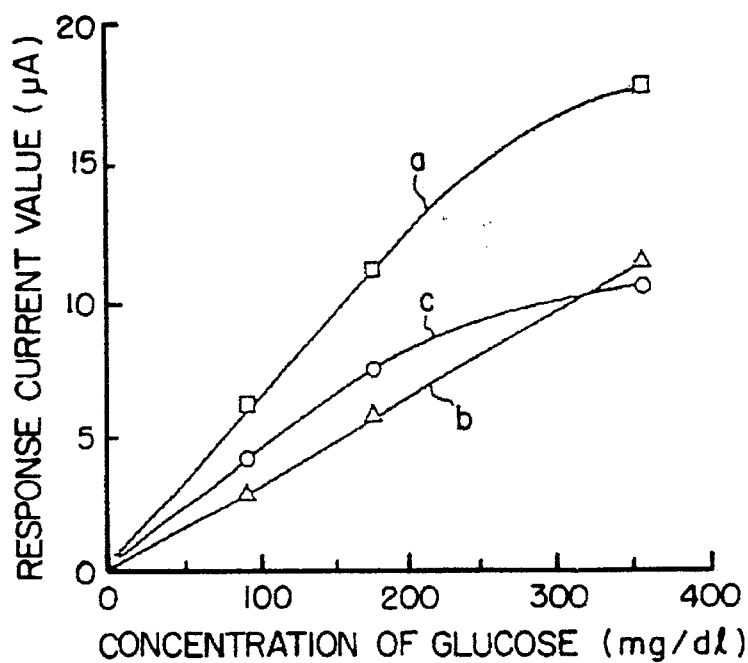
FIG. 4 is a graph showing the relationship between the concentration of glucose and a response current value obtained by biosensors according to an example and comparative examples of the invention; wherein a curve (a) shows the change of a response current value obtained by using a reaction layer including pyranose oxidase (hereinafter referred to as PyOx) and glucose oxidase (hereinafter referred to as GOD), a curve (b) shows the change of a response current value obtained by using a reaction layer including GOD alone, and a curve (c) shows the change of a response current value obtained by using a reaction layer including PyOx alone.

A biosensor of this invention comprises an electrically insulating substrate, an electrode system formed on the substrate which includes a working electrode and a counter electrode, and a reaction layer formed either on the substrate or above the substrate with a space therebetween.

The electrically insulating substrate is made from a plate of a synthetic resin such as polyethylene terephthalate, polyethylene, polyester, polypropylene, polystyrene, and polyvinyl chloride.

The electrode system including the working electrode and the counter electrode can be formed on the substrate by a known method. For example, after forming leads on the substrate, the working electrode and the counter electrode are formed so as to be connected to the respective leads and be insulated from each other. The materials for the leads and the electrodes can be any of known conductive materials such as carbon, silver, platinum, gold, and palladium.

The reaction layer used in the present biosensor includes a pyranose-oxidizing enzyme, which can simultaneously oxidize both α-glucose and β-glucose. An example of such a pyranose-oxidizing enzyme includes pyranose oxidase (EC1.1.3.10; PyOx).

The content of PyOx in the reaction layer of the present biosensor is preferably 1 to about 200 units, and more preferably about 2 to about 50 units per 1 $cm^2$ of the reaction layer. The term "unit" herein refers to the amount of an oxidoreductase necessary for oxidizing 1 μmol of glucose or polysaccharide in one minute. When the content of PyOx is smaller than 1 unit per 1 $cm^2$ of the reaction layer, an additional time of several minutes or more is required for the measurement. In addition, due to evaporation of a sample liquid during the additional time, the response current value can be affected. A content of PyOx exceeding about 200 units per 1 $cm^2$ of the reaction layer not only increases the production cost but also causes fluctuation in response current values because the reaction layer can be broken during the formation thereof.

The reaction layer can include glucose oxidase (EC1.1.3.4; GOD), in addition to the pyranose-oxidizing enzyme, in order to further improve the detection sensitivity against glucose in a sample liquid and to enable the glucose sensor to response to a wider range of glucose concentration. The content of GOD is preferably 1 to about 200 units per 1 $cm^2$ of the reaction layer. When GOD is used together with PyOx, the content of PyOx is preferably about 0.1 to about 200 units, and more preferably about 0.2 to about 40 units per 1 $cm^2$ of the reaction layer.

The reaction layer can further include various hydrophilic polymers. Examples of such hydrophilic polymer include carboxy methyl cellulose (hereinafter referred to as CMC), hydroxyethyl cellulose (HEC), hydroxypropyl cellulose (HPC), methyl cellulose, ethyl cellulose, ethyl hydroxyethyl cellulose, carboxymethyl ethyl cellulose, polyvinyl pyrrolidone, polyvinyl alcohol, polyamino acids such as polylysine, polystyrenesulfonic acid, gelatin or its derivatives, acrylic acid or its salts, methacrylic acid or its salts, starch or its derivatives, and maleic anhydride or its salt. In particular, CMC is preferred.

When a sample liquid including glucose is supplied to the reaction layer of the present biosensor, α-glucose and β-glucose in the sample liquid are respectively oxidized by the pyranose-oxidizing enzyme. Simultaneously, dissolved oxygen in the sample liquid is reduced into hydrogen peroxide. When a voltage is applied at this point, the hydrogen peroxide is oxidized. A response current generated in this oxidation is in proportion to the concentration of the hydrogen peroxide, i.e., the concentration of the substrate in the sample liquid. Thus, the concentration of the substrate in the sample liquid can be obtained by measuring the response current value.

In the present biosensor, the reaction layer can include an electron acceptor so as to form a reduced form of the electron acceptor simultaneously with the enzyme reaction, in stead of producing hydrogen peroxide simultaneously with the oxidation reaction of the substrate. Examples of the electron acceptor include a ferricyanide ion, p-benzoquinone or its derivatives, phenazine methosulfate, Methylene Blue, and ferrocene or its derivative. One or more of the electron acceptor can be used. In particular, a ferricyanide ion is preferred.

The content of the ferricyanide ion is preferably about 0.21 to about 3.30 mg, and more preferably about 0.30 to about 2.59 mg per 1 $cm^2$ of the reaction layer. When the content of the ferricyanide ion is smaller than about 0.21 mg per 1 $cm^2$ of the reaction layer, the measurable range of the glucose concentration can be extremely small. When the content of the ferricyanide ion exceeds about 3.30 mg per 1 $cm^2$ of the reaction layer, fluctuation of response current values can be caused because the reaction layer can be broken during the formation thereof, and the reliability of the biosensor can be degraded while it is stored.

The reaction layer used in the present biosensor can further include a polysaccharide hydrolase for hydrolyzing a polysaccharide to produce $\alpha$-glucose. The polysaccharide hydrolase is an enzyme capable of hydrolyzing a polysaccharide such as sucrose and maltose to produce glucose. Examples of such polysaccharide hydrolase include sucrose hydrolase such as invertase (hereinafter referred to as INV), maltose hydrolase such as maltase, and lactose hydrolase such as $\beta$-galactosidase. The content of the polysaccharide hydrolase is preferably 1 to about 400 units, and more preferably about 2 to about 200 units per 1 $cm^2$ of the reaction layer.

A production method for the present biosensor will now be described referring to FIGS. 1 and 2.

First, a conductive material such as silver paste is printed on an electrically insulating substrate 1 by screen printing, thereby forming leads 2 and 3. Then, another conductive material including a resin binder is printed on the substrate 1, thereby forming a working electrode 4, so as to be in contact with the lead 2.

Then, insulating paste is printed on the substrate 1, thereby forming an insulating layer 6. The insulating layer 6 covers the peripheral portion of the working electrode 4, so as to expose a fixed area of the working electrode 4. As is shown in FIG. 1, the insulating layer 6 also covers part of the leads 2 and 3. Around the working electrode 4 is formed a ring-shaped counter electrode 5 out of a conductive material including a resin binder. The counter electrode 5 is in contact with the lead 3. In this manner, an electrode system 8 including the working electrode 4 and the counter electrode 5 is formed on the substrate 1.

Alternatively, the present biosensor can comprise a three-electrode system formed on the substrate 1 including a reference electrode (not shown) in addition to the working electrode 4 and the counter electrode 5, for the purpose of further stabilizing the measurement accuracy.

A reaction layer is formed on the substrate 1 as follows:

An aqueous solution of the hydrophilic polymer is dropped and dried on the electrode system 8, thereby forming a hydrophilic polymer layer. Then, an aqueous solution including PyOx, and the electron acceptor and/or the polysaccharide hydrolase, if necessary, is dropped and dried on the hydrophilic polymer layer. For repeated application of the present biosensor, the pyranose-oxidizing enzyme, and the polysaccharide hydrolase, if necessary, can be immobilized on the hydrophilic polymer layer through crosslinking with glutaraldehyde or immobilized on the hydrophilic polymer layer together with a polymeric material such as nitrocellulose, cellulose acetate, and polyacrylonitrile. Furthermore, the electron acceptor can be chemically fixed on the hydrophilic polymer layer by using the polymeric material, if necessary. Thus, a reaction layer 7 covering the entire electrode system 8 as shown in FIG. 2 can be formed.

Alternatively, the reaction layer can be disposed above the substrate 1 with a space therebetween. In this case, as is shown in FIG. 3, the biosensor comprises the substrate 1 and a cover 30 disposed above the substrate 1 with a spacer 20 sandwiched therebetween. The cover 30 includes a hole 31 and a reaction layer 37 formed on one surface thereof. The cover 30 is disposed above the substrate 1 so as to oppose the reaction layer 37 and the electrode system 8 to each other. Such a reaction layer 37 disposed above the substrate 1 with a space therebetween can be formed as described in, for example, Japanese Laid-Open Patent Publication No. 1-114747. In this type of biosensor, when a sample liquid supplied through a sample supply port 38 reaches the space between the reaction layer 37 and the electrode system 8, the amount of hydrogen peroxide or a reduced form of the electron acceptor generated in the reaction layer 37 can be measured with the electrode system 8 as in the biosensor shown in FIG. 2.

The present biosensor can be used for quantitating various kinds of substrates included in a biological sample such as whole blood, plasma, serum, and urine, materials of the food industry and product thereof, for example fruit juice. When used for measuring a blood glucose level of a patient in particular, the present biosensor can serve as a disposable blood glucose sensor which can be easily used.

Examples

Specific examples of the present biosensor will now be described. It is noted that the invention is not limited to these examples. In the drawings mentioned in each example, a common reference numeral is used to refer to a common element, and the description is partly omitted for the sake of simplification.

Example 1

As an example of the present biosensor, a glucose sensor was manufactured as follows:

As is shown in FIG. 1, silver paste was printed by screen printing on an electrically insulating substrate 1 made of polyethylene terephthalate, thereby forming leads 2 and 3. Then, conductive carbon paste including a resin binder was printed on the substrate 1, thereby forming a working electrode 4, so as to be in contact with the lead 2.

Next, insulating paste was printed on the substrate 1, thereby forming an insulating layer 6. The insulating layer 6 covered the peripheral portion of the working electrode 4, so as to expose a fixed area of the working electrode 4.

Then, conductive carbon paste including a resin binder was printed on the substrate 1, thereby forming a ring-shaped counter electrode 5, so as to be in contact with the lead 3.

An aqueous solution of 0.5% by weight CMC was dropped on the electrode system 8, that is, the working electrode 4 and the counter electrode 5, and dried, thereby forming a CMC layer. A mixed aqueous solution including PyOx and potassium ferricyanide was dropped and dried on the CMC layer, thereby forming a reaction layer 7. The contents of PyOx and potassium ferricyanide in the reaction layer 7 were 10 units and 1.3 mg per 1 cm$^2$ of the reaction layer, respectively.

On the reaction layer 7 of the thus manufactured glucose sensor was dropped 90 mg/dl of aqueous glucose solution as a sample liquid. After one minute, a voltage of +0.5 V on the basis of a voltage at the counter electrode 5 was applied to the working electrode 4 and a current value was measured 5 seconds after the voltage application. In this manner, a response current value to the glucose solution was measured twelve times in total by using a fresh glucose sensor in each measurement. Fluctuation in the obtained response current values was small.

Furthermore, response current values were measured with regard to 180 mg/dl and 360 mg/dl of aqueous glucose solutions also twelve times, respectively in the same manner as described above. The thus obtained response values were found to be increased as the glucose concentration was increased, and the increase ratio was large.

As a comparative example, a glucose sensor including glucose oxidase (EC1.1.3.4; GOD) instead of PyOx was manufactured, and a response current value was measured twelve times with regard to the glucose solutions having the above-mentioned concentrations. The obtained response current values were fluctuated in the same glucose concentration. In addition, although the response current values were found to be increased as the glucose concentration was increased, the increase ratio was small.

Example 2

As an example of the present biosensor, a sucrose sensor was manufactured as follows:

In the same manner as in Example 1, leads 2 and 3, an electrode system 8 (i.e., a working electrode 4 and a counter electrode 5), and an insulating layer 6 were formed on an electrically insulating substrate 1 made of polyethylene terephthalate. Then, an aqueous solution of 0.5% by weight CMC was dropped and dried on the electrode system 8, thereby forming a CMC layer.

A mixed aqueous solution including PyOx, INV, and potassium ferricyanide was dropped and dried on the CMC layer, thereby forming a reaction layer 7. The contents of PyOx, INV, and potassium ferricyanide in the reaction layer 7 were 10 units, 40 units and 1.3 mg per 1 cm$^2$ of the reaction layer, respectively.

When 171 mg/dl of aqueous sucrose solution as a sample liquid was dropped on the reaction layer 7 of the thus manufactured sucrose sensor, the reaction layer 7 was dissolved by the sample liquid. After 3 minutes, a voltage of +0.5 V on the basis of a voltage at the counter electrode 5 was applied to the working electrode 4, and a current value was measured 5 seconds after the voltage application.

Furthermore, response current values were measured with regard to 342 mg/dl and 684 mg/dl of aqueous sucrose solutions by using a fresh sucrose sensor in each measurement in the same manner as described above.

The obtained response current values were found to be increased as the sucrose concentration was increased, and the increase ratio was large.

As comparative examples, a maltose sensor and a lactose sensor were manufactured in the same manner except that INV was replaced with maltose hydrolase and lactose hydrolase, respectively. These maltose and lactose sensors exhibited the same effect as described above.

Example 3

As an example of the present biosensor, a glucose sensor was manufactured as follows:

In the same manner as described in Example 1, leads 2 and 3, an electrode system 8 (i.e., a working electrode 4 and a counter electrode 5), and an insulating layer 6 were formed on an electrically insulating substrate 1 made of polyethylene terephthalate. Then, an aqueous solution of 0.5% by weight CMC was dropped and dried on the electrode system 8, thereby forming a CMC layer.

A mixed aqueous solution including PyOx, GOD, and potassium ferricyanide was dropped and dried on the CMC layer, thereby forming a reaction layer 7. The contents of PyOx, GOD, and potassium ferricyanide in the reaction layer 7 were 1 unit, 10 units, and 1.3 mg per 1 cm$^2$ of the reaction layer, respectively.

On the reaction layer 7 of the thus manufactured glucose sensor was dropped 90 mg/dl of aqueous glucose solution as a sample liquid. After 1 minute, a voltage of +0.5 V on the basis of a voltage at the counter electrode 5 was applied to the working electrode 4, and a current value was measured 5 seconds after the voltage application.

Furthermore, response current values were measured with regard to 180 mg/dl and 360 mg/dl of aqueous glucose solutions by using a fresh glucose sensor in each measurement in the same manner as described above. The response characteristic between glucose concentrations and response current values is shown in FIG. 4 as a curve (a).

As comparative examples, a glucose sensor not including PyOx and a glucose sensor not including GOD were respectively manufactured, and the response current values were measured in the same manner as described above. The results are shown in FIG. 4 as curves (b) and (c).

As is shown in FIG. 4, the glucose sensor including GOD alone as the enzyme (corresponding to curve (b) in FIG. 4) exhibited the lowest response current values because the response current values depend upon the concentration of only the β-glucose included in the sample liquid. In contrast, the glucose sensor including PyOx alone as the enzyme (corresponding to curve (c) in FIG. 4) exhibited higher current values than curve (b) especially when the glucose concentration was low because the response current values depend upon the sum of the concentrations of α-glucose and β-glucose included in the sample liquid. However, the glucose sensor including PyOx alone as the enzyme exhibited lower current values than curve (b) when the glucose concentration was high. As a result, the glucose sensor including both PyOx and GOD (corresponding to curve (a) in FIG. 4) constantly exhibited high response current values in the widest concentration range.

Example 4

As an example of the present biosensor, a sucrose sensor was manufactured as follows:

In the same manner as in Example 1, leads 2 and 3, an electrode system 8 (i.e., a working electrode 4 and a counter electrode 5), and an insulating layer 6 were formed on an electrically insulating substrate 1 made of polyethylene terephthalate. Then, an aqueous solution of 0.5% by weight CMC was dropped and dried on the electrode system 8, thereby forming a CMC layer.

A mixed aqueous solution including PyOx, GOD, INV, and potassium ferricyanide was dropped and dried on the CMC layer, thereby forming a reaction layer 7. The contents of PyOx, GOD, INV, and potassium ferricyanide in the reaction layer 7 were 1 unit, 10 units, 40 units, and 1.3 mg per 1 cm$^2$ of the reaction layer 7, respectively.

When 171 mg/dl of aqueous sucrose solution was dropped on the reaction layer 7 of the thus manufactured sucrose sensor, the reaction layer 7 was dissolved by the sample liquid. After 3 minutes, a voltage of +0.5 V on the basis of a voltage at the counter electrode 5 was applied to the working electrode 4, and a current value was measured 5 seconds after the voltage application.

Furthermore, response current values were measured with regard to 342 mg/dl and 684 mg/dl of aqueous sucrose solutions by using a fresh sucrose sensor in each measurement in the same manner as described above.

The obtained response current values were found to be increased as the sucrose concentration was increased, and were constantly high in a wide range of the sucrose concentration.

As a comparative example, a sucrose sensor was manufactured in the same manner as described above except that GOD was excluded from the reaction layer 7, and response current values were similarly measured. The obtained response current values were constantly lower than those obtained by the sucrose sensor including GOD.

A maltose sensor and a lactose sensor manufactured by respectively using maltose hydrolase and lactose hydrolase instead of INV were found to exhibit the same effect as described above.

Example 5

A biosensor was manufactured in the same manner as in Examples 1 to 4 except that potassium ferricyanide was not included in the reaction layer 7. Sample liquid having various substrate concentrations as in Examples 1 to 4 were respectively dropped on the electrode system of these biosensors. After a predetermined time, a voltage of +1.0 V on the basis of a voltage at a counter electrode 5 was applied to a working electrode 4, and a current value was measured 5 seconds after the voltage application.

The obtained response current values were found to be increased as the concentration of the substrate was increased.

Example 6

A glucose sensor was manufactured in the same manner as in Example 3.

Whole blood having a glucose concentration of 95 mg/dl was dropped as a sample liquid on a reaction layer 7 of this glucose sensor. After 1 minute, a voltage of +0.5 V on the basis of a voltage at a counter electrode 5 was applied to a working electrode 4, and a current value was measured 5 seconds after the voltage application.

Furthermore, response current values were measured with regard to whole blood having glucose concentrations of 170 mg/dl and 320 mg/dl by using a fresh glucose sensor in each measurement in the same manner as described above. The response characteristic between glucose concentrations and response current values is shown as a curve (a) in FIG. 5.

As comparative examples, a glucose sensor not including PyOx and a glucose sensor not including GOD were respectively manufactured, and response current values were measured in the same manner. The results are shown as curves (b) and (c) in FIG. 5.

Figure 5:
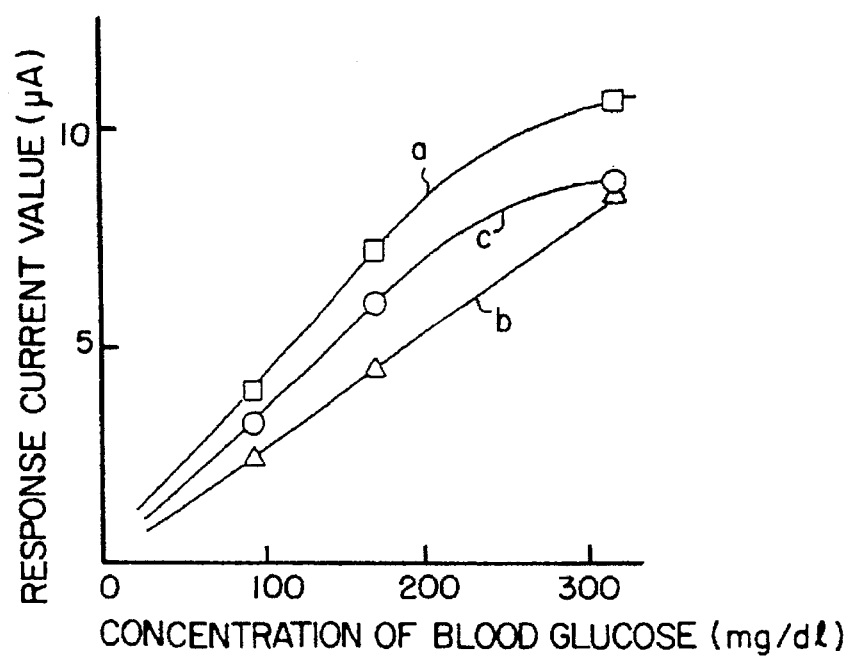
FIG. 5 is a graph showing the relationship between the concentration of blood glucose and a response current value obtained by glucose sensors according to an example and comparative examples of the invention; wherein a curve (a) shows the change of a response current value obtained by using a reaction layer including PyOx and GOD, a curve (b) shows the change of a response current value obtained by using a reaction layer including GOD alone as an oxidoreductase, and a curve (c) shows the change of a response current value obtained by using a reaction layer including PyOx alone.

As is shown in FIG. 5, the glucose sensor including GOD alone as the enzyme (corresponding to curve (b) in FIG. 5) exhibited the lowest response current values because the current values depend upon the concentration of only the β-glucose in the whole blood. In contrast, the glucose sensor including PyOx alone as the enzyme (corresponding to curve (c) in FIG. 5) exhibited higher response current values than curve (b) because the current values depend upon the sum of the concentrations of α-glucose and β-glucose in the whole blood. As a result, the glucose sensor including both PyOx and GOD (corresponding to curve (a) in FIG. 5) exhibited constantly high response current values in the widest range of the blood glucose concentration.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A biosensor comprising:
   an electrically insulating substrate;
   an electrode system formed on the substrate which includes a working electrode and a counter electrode; and
   a reaction layer formed on the substrate or above the substrate with a space therebetween,
   wherein the reaction layer includes a pyranose-oxidizing enzyme and glucose oxidase (EC1.1.3.4).

2. A biosensor according to claim 1, wherein the pyranose-oxidizing enzyme is pyranose oxidase (EC1.1.3.10).

3. A biosensor according to claim 1, wherein the reaction layer further includes an electron acceptor.

4. A biosensor according to claim 3, wherein the electron acceptor is a ferricyanide ion.

5. A biosensor according to claim 4, wherein contents of the pyranose-oxidizing enzyme, the glucose oxidase, and the ferricyanide ion are about 0.1 to about 200 units, 1 to about 200 units, and about 0.21 mg to about 3.30 mg, respectively per 1 $cm^2$ of the reaction layer.

6. A biosensor according to claim 1, wherein the reaction layer further includes a polysaccharide hydrolase.

7. A biosensor according to claim 6, wherein the polysaccharide hydrolase is one selected from the group consisting of sucrose hydrolase, maltose hydrolase, and lactose hydrolase.

8. A biosensor according to claim 1, wherein a content of the pyranose-oxidizing enzyme is 1 to about 200 units per 1 $cm^2$ of the reaction layer.

9. A biosensor according to claim 1, wherein a content of the pyranose-oxidizing enzyme is about 0.1 to about 200 units per 1 $cm^2$ of the reaction layer.

10. A biosensor according to claim 1, wherein the biosensor is used for measuring a blood glucose level.

11. A biosensor for quantitating a biochemical substrate included in a sample liquid by reducing an electron acceptor with an electron generated through an enzyme reaction of the biochemical substrate and electrochemically measuring an amount of a reduced form of the electron acceptor, comprising:
    an electrically insulating substrate;
    an electrode system formed on the insulating substrate and including a working electrode and a counter electrode; and
    a reaction layer formed on the insulating substrate or above the substrate with a space therebetween,
    wherein the reaction layer includes a pyranose-oxidizing enzyme, an electron acceptor, and glucose oxidase (EC1.1.3.4).

12. A biosensor according to claim 11, wherein the biosensor is a glucose sensor.

13. A biosensor according to claim 11, wherein the biosensor is used for measuring a blood glucose level.

* * * * *